United States Patent [19]

Schrämmli et al.

[11] Patent Number: 4,961,646
[45] Date of Patent: Oct. 9, 1990

[54] MANUAL DEVICE FOR THE DETECTION OF OPTICAL REFLECTION PROPERTIES

[75] Inventors: Fortunat Schrämmli, Hausen; Markus Berner, Niederhasli; Hans Ott, Regensdorf, all of Switzerland

[73] Assignee: Gretag Aktiengesellschaft, Regensdorf, Switzerland

[21] Appl. No.: 300,929

[22] Filed: Jan. 24, 1989

[30] Foreign Application Priority Data

Feb. 2, 1988 [CH] Switzerland ............................ 361/88

[51] Int. Cl.$^5$ ............................ G01J 3/18; G01J 3/42; G01N 21/27
[52] U.S. Cl. .................................... 356/328; 356/448
[58] Field of Search ................ 356/328, 334, 445–448; 250/226

[56] References Cited

U.S. PATENT DOCUMENTS

| | | | |
|---|---|---|---|
| 3,244,062 | 4/1966 | Sweet | 356/446 |
| 3,923,399 | 12/1975 | Brumley | 356/328 |
| 3,982,824 | 9/1976 | Rambauske | 350/294 |
| 4,025,200 | 5/1977 | Zeineh . | |
| 4,053,235 | 10/1977 | Hampton | 356/418 |
| 4,076,421 | 2/1978 | Kishner | 356/328 |
| 4,078,858 | 3/1978 | Mast | 356/446 |
| 4,093,991 | 6/1978 | Christie, Jr. et al. | 356/328 |
| 4,645,350 | 2/1987 | Weidmann et al. | 356/418 |
| 4,756,619 | 7/1988 | Gerlinger et al. | 356/328 X |
| 4,802,763 | 2/1989 | Gerlinger et al. | 356/328 X |
| 4,865,456 | 9/1989 | Mast et al. | 356/446 |
| 4,895,419 | 1/1990 | Doyle et al. | 350/3.69 |

FOREIGN PATENT DOCUMENTS

| | | |
|---|---|---|
| 0242725 | 10/1987 | European Pat. Off. . |
| 3313668 | 10/1984 | Fed. Rep. of Germany . |
| 1527717 | 7/1968 | France . |
| 2181265 | 4/1987 | United Kingdom . |

OTHER PUBLICATIONS

Eine Einfache Messanordnung zur Photoelektrischen Spektrometrie Moglichst Kleiner Konzentrationen, M. Nordmeyer, Spectrochimica Acta, vol. 27B, No. 8, Aug. 1972, Pergamon Press (Northern Ireland).
Proceedings of the Society of Photo-Optical Instrumentation Engineers, vol. 240, "Periodic Structures, Gratings, Moire Patterns, and Diffraction Phenomena", Jun. 29–Aug. 1, 1980, San Diego, J. M. Lerner, Diffraction Gratings Ruled and Holographic-a Review, pp. 82–88.
Unterscheiden Kleinste Differenzen, H. Hencke, Feb. 27, 1987, pp. 29–39.
Patent Abstract of Japan, vol. 11, No. 370 (P642) (2817), Dec. 3, 1987—"Photoelectric Colorimeter Which Can Measure Density"—Japanese Patent Pub. No. 62-142240, Jun. 25, 1987.
Nouvelles Graphiques, vol. 37, No. 2, Jan. 1987, "La Nature Connait Ses Imperfections", Macbeth y pallie.

*Primary Examiner*—Vincent P. McGraw
*Attorney, Agent, or Firm*—Burns, Doane, Swecker & Mathis

[57] ABSTRACT

A manual device for the detection of photometric data which includes a measuring head to illuminate a measuring surface and to detect the light reflected. The measuring light captured by the measuring head is spectrally decomposed by a monochromator containing a diffraction grating. The intensity of the light exiting through an outlet diaphragm is detected by a photodetector. The spectral position of the measuring light is set by a drive motor rotating a grating shaft connected with the holder of the diffraction grating. From the spectra detected, densitometric and colorimetric data are calculated by a computer, which together with the spectra determined, may be displayed on a display field.

26 Claims, 3 Drawing Sheets

MANUAL DEVICE FOR THE DETECTION OF OPTICAL REFLECTION PROPERTIES

BACKGROUND OF THE INVENTION

The invention relates to a manual device for the detection of photometric data which includes a measuring head, a source of light, optical illumination means to illuminate a measuring surface to be examined by the manual device, optical measuring means to capture the measuring light reflected by the measuring surface, and an optoelectronic layout exposed to the measuring light for the conversion of optical signals into data that may be displayed by a display unit.

A reflecting manual densitometer for the graphical industry is known from U.S. Pat. No. 4,645,350 and makes it possible to illuminate by means of a projecting measuring head a measuring surface and to determine the intensity of the light reflected by the measuring surface after its passage through a selectable measuring filter, in order to determine the reflectivity or density of a printing ink. The replaceable measuring filters are located in a filter wheel, which may be rotated with the aid of a motor so that all four measuring filters present may be introduced into the path of the measuring beam. In this manner the densitometer may be used for four different spectral ranges.

From German Patent Publication No. 3,313,668 a color measuring device is known, in which the measuring head and an evaluating unit are combined in a single structural unit, with a rechargeable energy source as the power supply. By the combination of these two components in a single structural unit without a connecting cable between the measuring head and the evaluating unit a certain miniaturization and easier handling are obtained.

However, the known color measuring device is relatively voluminous and greatly restricted in its applications. To recharge the source of power, it is set onto a charger, which together with the unit formed by the measuring head and the evaluating unit constitutes a single separable unit.

European Patent Publication No. 0,242,725 describes a spectral photometer, which may be located at a large distance from the measuring surface and which includes a source of light with its associated illumination optics as a first structural unit, and which evaluates the reflected light by means of a second structural unit. Although both units are located in a single housing adjacent to each other, in view of the large distance to the measuring surface desired, a particularly compact configuration of the second unit is not important; said second unit containing a polychromator with a diffraction grating. Because the diffraction grating is in the form of a planar diffraction grating, optical collimator means are required between the grating and a row of photodiodes. In place of the row of photodiodes a single photodiode may also be provided, if the dispersive element is variable. The dispersive element, which is in the form of a diffraction grating or a prism, is provided on the side of light incidence with collimator optics, so that the known polychromator is relatively large in view of the collimator optics and is not suitable for a manual device.

Holographically produced concave reflection gratings are known from "Proceedings of the Society of Photo-Optical Instrumentation Engineers", Vol. 24U, Periodic Structures, Gratings, Moire Patterns and Diffraction Phenomena, Jul. 29–Aug. 1, 1980, San Diego, S.P.I.E., 1980, (Bellingham, Washington, U.S.), J. M. Lerner, "Diffraction Gratings, Ruled and Holographic—a Review", pages 82–88. How such gratings may be used in the miniaturization of a manual device for the determination of optical reflection properties, is not described or discussed in the review article.

U.S. Pat. No. 4,093,991 discloses a spectral photometer with a monochromator, the outlet light of which supplies an optical sensor connected with a microcomputer comprising a keyboard. As an integration sphere is associated with the source of light and the monochromator, the configuration of the optical components is rather voluminous. The monochromator is connected with a coding device which makes it possible for the microcomputer to carry out a digital wavelength selection. The monochromator has a disk shaped interference wedge filter, the rotating position of which is correlated with the wavelength chosen. Together with the lens layout preceding and following it, a voluminous unit is obtained, which is suitable for laboratory use, but not for a miniaturized manual device.

In the article by M. Nordmeyer: "A simple measuring layout for the photoelectric spectrometry of the smallest possible concentrations", published in Spectrochimica Acta, Vol. 27B, No. 8, August 1972, Pergamon Press (Northern Ireland), an electronic circuit and an alternating method are described, whereby signal intensities at the location of a spectral line and of a representative underground location are measured photoelectrically and alternatingly. The electric circuit to carry out the alternating method contains two integrators.

In Elektrotechnik, Vol. 69, No. 3, Feb. 27, 1987 (Wurzburg), H. Hencke: "Distinction of very small differences", pages 28–38, a specially developed color sensor is described, which is capable of working very accurately and rapidly on a conveyor. The color sensor comprises an optical system which emits a white light to a measuring object and a red-green-blue photodiode receiving the light reflected by the measuring surface of the object, in order to produce an electrical analog signal. A control device is correlated with the color sensor; it contains a serial communication interface whereby for example the degree of browning of ceramic disks may be controlled by the color sensor.

A photoelectric color measuring device to determine color and density values is known from Patent Abstracts of Japan, Vol. 11, No. 370 (P-642) (2817), Dec. 3, 1987 and Japanese Patent Publication No. 62-142,240 (MINOLTA CAMERA CO.,LTD), Jun. 25, 1987. The photoelectric color measuring device contains a layout including a computer to process the data detected by the sensor unit. Different memories are provided for programs, color conversions and the storage of color and density information.

From Nouvelles Graphiques, Vol. 37, No. 2, January 1987 (Deurne, Antwerpen, BE), "La nature connait ses imperfections (Nature knows its imperfections), Macbeth y pallie", p. 2, a portable and automatic manual densitometer is known, which comprises a computer, the programs of which make it possible to identify the color measured, the type of measuring surface and the paper used.

With this known manual device only densitometric evaluations are possible, but no determination of colorimetric values are possible.

SUMMARY OF THE INVENTION

It is the object of the present invention to improve a manual device of the known type so that the limitations imposed by the changing of given measuring filters relative to the photometric data that may be determined, are largely avoided.

This object is attained according to the invention by a manual device for the determination of optical reflection properties with a measuring head which includes an optoelectronic layout having a device for the spectral decomposition of a measuring light, equipped through a monochromator with a holographic concave reflection grating, together with a layout for the detection and evaluation of the spectrum of the measuring light.

BRIEF DESCRIPTION OF THE DRAWINGS

Other objects and advantages of the present invention will become apparent from the following detailed description of the preferred embodiments as described in conjunction with the accompanying drawings in which.

DETAILED DESCRIPTION OF THE PREFERRED EMBODIMENTS

Figure 1:
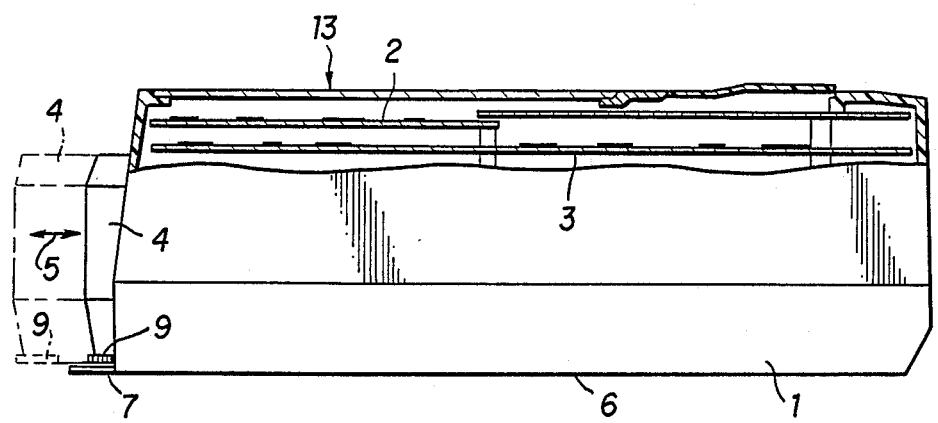
FIG. 1 shows a partial, cross-sectional, lateral elevation of the manual device according to the invention.

The device shown in FIG. 1 in a partial, cross-sectional, lateral elevation corresponds in its external dimensions to a reflecting manual densitometer and has an appropriately compact configuration. But in contrast to a conventional densitometer, the manual device shown in FIG. 1 makes it possible to determine in addition to densitometric values, also reflection and density spectra, together with colorimetric data.

The manual device comprises a housing 1, in which one or several printed circuit boards 2, 3 are located for a measured value processing and control logic; this is indicated schematically in the top part of the sectioned housing 1.

A measuring head 4 projects from the left lateral wall of the housing 1; it may be displaced between a rest position shown in FIG. 1 by solid lines, and a working position shown by broken lines, along the double arrow 5 parallel to the bottom 6 of the housing 1. In the retracted rest position a sight plate 7 projects over the edge of the measuring head 4, which is seen particularly clearly in FIG. 2. The sight plate 7 contains a measuring diaphragm 8 serving to indicate the position and size of the measuring spot of the head 4 in its working position and to shield it from scatter light.

Figure 2:
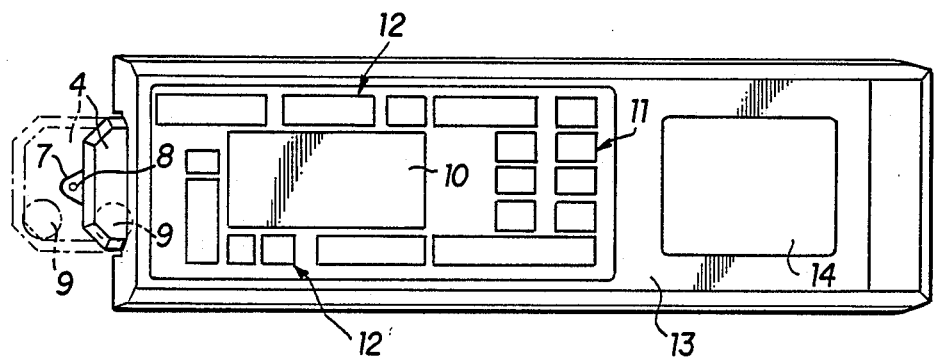
FIG. 2 shows a top view of the manual device.

When the measuring head 4 has been extended from its rest position shown in FIGS. 1 and 2 by solid lines, into the working or measuring position shown in FIGS. 1 and 2 by broken lines, the optically effective axis of the measuring head 4 passes exactly through the center of the measuring diaphragm 8.

In FIGS. 1 and 2 a filter wheel drive 9 is seen, which engages a filter wheel provided in the measuring head 4 and makes it possible to insert into the beam path of the measuring head 4 a polarizer for the measurement of wet printed sheets, a D65 conversion filter to take into consideration fluorescence, or a diaphragm without a filter, as desired. The filter wheel drive 9 thus has three manually set positions, which may be displayed on a display field 10, for example a liquid crystal display.

The display field 10 also serves to indicate the measured values determined by the manual device in numerical form or in the form of spectra or bar diagrams. To operate the manual device, a row of keys of a keyboard 11 are provided around the display 10, together with several indicating fields 12 correlated with the display field 10. The display field 10, the keyboard and the indicating fields 12 are located on the top side 13 of the housing 1, with a measuring key 14 having a large surface area being provided on the side facing away from the measuring head 4 for the actuation of a measuring process.

Figure 3:
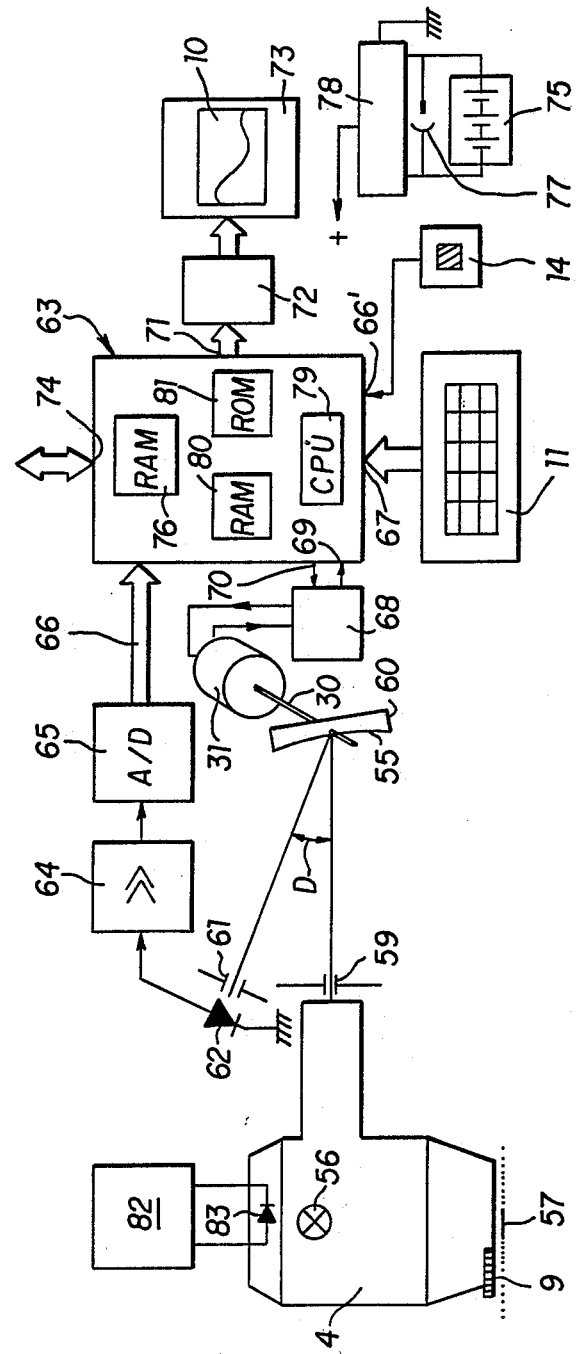
FIG. 3 shows a schematic view of the optical and electronic components of the manual device; and, FIG. 4 shows a block diagram of an analog/digital converter to digitalize the intensity of the measuring light and of the lamp light in the measuring head of the manual device.

Upon actuation of the measuring key 14, the processing and control logic is made to move the measuring head 4 from its rest position into the working position, in order to detect by means of a spectral chamber provided inside the housing 1, together with a diffraction grating 55 shown in FIG. 3, the spectrum of the light reflected for example by a printed sheet upon which the manual device is resting, at the location of the measuring diaphragm. The reflection spectrum is processed by means of the processing and control logic. Following the detection of the spectrum, the measuring head 4 returns into its rest position, until a new measuring process is actuated by the measuring key 14.

The measuring head 4 is displaced by means of the measuring carriage, not shown, which is guided inside the housing 1 in a longitudinally displaceable manner.

The measuring head 4 is shown in FIG. 3, together with a series of optical, optoelectronic, electronic and mechanical structural parts. It is assumed in the following that the measuring head 4 has been advanced into its measuring position and that a lamp 56 located in the measuring head 4 illuminates a measuring spot 57 having a diameter of 3 mm, at an angle of 45°. In addition to the lamp 56, the measuring head 4 contains a number of optical components, not shown in the drawing. The light reflected by the measuring spot 57 perpendicularly upwards is collected at an angle of about 5° and evaluated. The display field 10 shows, together with the correlated indicator field 12, the type of light selected, in particular type A, type C or type D65. The aforementioned filter wheel position selected, i.e. no filtering, polarization or D65 conversion filter, are also indicated. The filter position of the filters located in the measuring head 4 and displaced by means of the filter wheel drive 9 is, as mentioned above, also indicated on the display field 10.

The filter not shown in the drawing must be placed into the position desired prior to measuring. Measurements with the crossed polarizer provided yield the same results on wet and dry printed sheets. This process, which is already known from densitometry is used in the device described in connection with colorimetry also.

Upon the insertion of the D65 conversion filter, the filter converts the lamp light (light type A) to daylight (Type D65). The manual device therefore also makes possible the correct measuring of fluorescent colors. The filter wheel position in which D65 filtering is in effect, is intended primarily for use in colorimetry.

The light reflected by the measuring spot 57 on the surface being examined and detected by the measuring head 4 arrives in the spectral chamber, which contains a holographic monochromator with the diffraction grating 55. The diffraction grating 55 serves to spectrally decompose the light incident through the inlet slit 59 with a width of 0.75 mm and is in the form of, for example, a holographic concave reflection grid with 1250 lines/mm, which is optimized relative to its efficiency for blue. The components correlated with the diffraction grating 55 form a variable monochromator. The diffraction grating 55 is supported in a holder 60 fastened to a grating shaft 30, which may be rotated by means of a drive motor 31. The drive motor 31 is shown for the sake of clarity to be directly connected with the grafting shaft 30, although in the exemplary embodiment described a reduction gear is provided to enable a highly precise, reproducible grating position to be set. The grating shaft 30 extends at right angles to the plane of incidence defined by the light entering through the inlet slit 59 and the light exiting through the outlet slit 61, which again is 0.75 mm wide. The angle D between the inlet and the outlet beam amounts to for example 25°.

The monochromatic light exiting through the outlet slit 61 impacts a photodiode 62, which converts the optical signal into an electrical signal.

Depending on the intensity of the light reflected by the measuring spot 57 within the spectral range set, a photocurrent of greater or lesser intensity is produced in the photodiode 62. The resolution of the monochromator constructed with the aid of the diffraction grating 55 and the properties of the other structural parts are chosen so that spectral support locations spaced apart 10 nm may be processed over the entire visible range of 380 to 730 nm. In this manner, the manual device makes it possible to measure a reflection spectrum or a density spectrum with 36 support locations. The intensities determined during the scanning of the entire spectrum by the photodiode 62 are used to calculate all of the measuring functions of the device by means of a computer 63.

The photodiode 62 is connected with the inlet of an amplifier 64 which supplies an analog/digital converter 65, wherein the analog values detected by the photodiode 62 are digitalized for processing in the computer 63. The outlet of the analog/digital converter 65 is connected through a bus 66 with an inlet of the computer 63.

In addition to the inlet for the data of the analog/digital converter 65, the computer 63, which represents a part of the aforementioned processing and control logic, has additional inlets for the rest of the peripheral electronics. In particular, an inlet 66, is seen in FIG. 3, through which a start signal is triggered for a measuring process by actuating the measuring key 14. The keyboard 11 for the direct operation of the manual device is connected with a keyboard inlet 67 of the computer 63. The drive motor 31 is associated with motor electronic means 68, which through a position inlet 69, in particular in the case of an absolute position determination of the drive motor 31, pass the data obtained to the computer 63.

The motor electronics 68 are used on the one hand to actuate the motor, and on the other, to determine the absolute position. The motor positioning of the drive motor 31 must be very accurate, as the position of the diffraction grating 55 and the momentarily selected spectral range depend on it. The drive motor 31 is a dc motor, the motor rpm of which is controlled by means of a phase-lock loop (PLL) circuit. The desired frequency is supplied by the quartz of the microprocessor 79 contained in the computer 63, wherein the quartz frequency is subdivided by a timer in the processor. The actual frequency is supplied by an incremental transmitter on the drive motor 31 with 120 increments per revolution. The quartz accurate revolution of the drive motor is thereby assured.

The specific type of phase detector, which is in the form of an automatic synchronous phase detector, makes it further possible to detect certain error conditions, such as for example a single "miss" of the PLL, in a reliable manner.

For the detection of the absolute position of the grating drive, light barriers, not shown, are used, the emitter disks of which are correlated with different shafts of the gear, not shown, between the drive motor 31 and the grating shaft 30. The light barriers and the emitter disks make possible the accurate detection of the motor position and thus of the position of the grating. While the feedback concerning the motor position is effected through the position inlet 69, the motor electronics 68 are actuated through the motor outlet 70 of the computer 63, together with the drive motor 31.

In addition to the motor outlet 70, the computer 63 has a data outlet 71 connected with the display control 72, which in turn supplies a display unit 73 containing the display field 10. The display field 10 is a liquid crystal fully graphical point matrix display with $64 \times 128$ points. The keyboard contains ten keys for the direct operation of the device, in addition to the measuring key 14 for the actuation of measurements.

But the manual device may be operated directly not only by the keyboard 11, but also remotely through a serial interface 74, for which a bushing is provided on the side opposite to the measuring head of the housing shown in FIGS. 1 and 2, and which operates bi-directionally, so that the device may be operated by remote control.

The serial interface 74 is similar to a standard RS 232 and makes it possible to actuate all of the functions which normally are selected manually through the keyboard 11, by remote control through a cable connected with said serial interface 74. The serial interface 74 makes it further possible to read out measured results and in particular to pass a result to a printer.

The manual device is operated by means of a battery 75, shown schematically in FIG. 3 and optionally located in the housing 1 in the vicinity of the bushing for the serial interface. The battery 75 may be recharged by means of a charging bushing 77, which is again located on the side opposite to the measuring head 4 of the housing 1. To save the battery 75, a direct supply of power from an external source is alternatively possible. The voltages required by the different parts of the device are produced by a cycling voltage transformer 78 in order to assure optimal efficiency and thus the lowest possible thermal loss. In addition, a large number of possible measuring processes are thereby obtained with a single charge of the battery. In order to save power, the principal current is shut down after any action whereby the measuring head 4 is extended from or retracted into the housing 1. The principal current source is active for only 0.1 to 1.5 seconds after any such action. The data determined by such a measurement and the values obtained from such data are displayed by the display field 10 for about 30 seconds, for which the display unit 73 remains active longer and is supplied with power for example for another 30 seconds. The keyboard 11, the serial interface 74 and a permanent RAM 76 are always under power, so that the device may be reactivated and the data are not lost. The clean actuation and reactivation is controlled by a synchronous state automatic device and several analogous monitoring switches, which are not shown separately in FIG. 3.

The computer 63 shown schematically in FIG. 3 has a central processor unit CPU 79 and a plurality of direct access memories, in the aforementioned non-volatile RAM 76 and a volatile RAM 80 and a constant value memory or ROM 81. The memories serve on the one hand to temporarily store intermediate results, and on the other, to permanently store programs, tables, standardizing curves and the like.

The computer 63 calculates from the spectra obtained by means of the measuring head 4 and the monochromator containing the diffraction grating 55, with consideration of possible correction data, all output data of the manual device. For this reason, the manual device described is not only compact, but also constitutes a highly universal reflecting manual spectrometer for the graphical industry, which both evaluates and interprets the photometric data determined. By means of stored programs, the device makes it possible to not only determine the conventional densitometric data, but also to determine spectra, together with colorimetric values. In the process, comparative measurements with different reference values stored in the RAM 76, may also be carried out. Furthermore, the measurements may be related to different whites, i.e. absolute white and paper white. It is further possible to measure with polarized and approximate D65 light.

The computer 63 controls on the one hand the drive of the grating shaft 30 and thus the drive of the diffraction grating 55, and on the other hand, the runout and retraction of the measuring carriage, on which the measuring head 4 is mounted, together with its correlated components. In particular, the analog/digital converter 65 is located on the mobile measuring system.

The keyboard 11 comprises a data protection key, which must be actuated in order to carry out certain functions which must not be selected by mistake. If the measuring key 14 is actuated, the device carries out a spectral measurement, even if only a densitometric evaluation is intended. Independently of the evaluation to be effected after the determination of the spectral data, wherein several evaluations are possible on the basis of the same data, the computer 63 calculates all measuring functions from the spectrum determined. All of the functions may also be selected and displayed after the measurement itself.

By means of the programs stored in the computer 63 it is possible to process both the reflection spectra and the density spectra and to display them on the display field 10. Due to the spectral measurements, the device makes it possible to carry out arbitrary densitometric measuring functions. For this purpose, from the spectrum the conventional densitometric values are calculated by formulas known to those skilled in the art. The computer 63 is able to determine by means of stored, standard filter characteristics, standard densities for different printing inks (black, cyan, magenta, yellow).

The spectra stored in the computer 63 permit it to automatically select an electronically stored filter without a mechanically moved filter and to continue to operate with it. In this manner, it is possible to carry out with the above described device, automatic color recognitions of print-technical scale inks.

While for mechanical filters relatively large amounts of space and expense must be invested, it is possible by means of the computer 63 to store a series of different filter standards and to select them with the keyboard 11. In particular, filter characteristics according to ANSI A, ANSI T and DIN 16536 are stored in the ROM 81. Densities may be calculated according to one or the other standard, as needed. It should be emphasized here that for any recalculation according to another standard it is not necessary to move any mechanical parts, as by moving the diffraction grating 55, the entire spectral range is being scanned.

The program stored in the computer 63 makes it further possible to measure maximum densities within the spectral range covered. In the process, on the one hand the density, and on the other hand, the spectral position of the density maximum are determined and displayed. Conventional densitometers cannot indicate such values. The maximum density may be interpreted in a number of ways. Firstly, it represents the maximum value of the density spectrum. Secondly, its value corresponds to a measurement of density by means of a narrow band filter, the passage range of which has exactly the wavelength at which the ink to be measured has the highest density. It also represents a density measurement with a narrow band filter automatically adapting itself to the color being measured in an optimal manner.

As mentioned above, the device is capable of performing colorimetric measurements. Based on the programs stored, the following colorimetric values may be displayed: xyY, L*,C*h*(ab) and L*u*v*. Within the range of the colorimetric measuring functions, an angle of observation between 2° and 10° and light types A, C or D65 may be chosen.

The memories provided in the computer 63 make it possible to carry out comparative measurements in an elegant manner, in which the measured values are compared with stored reference values for quality control.

This is possible with the aforedescribed device for all measuring functions, i.e. for spectra, densitometric values and colorimetric values. The reference values are either measured and stored reference values, or values entered manually. Each of the reference values consists of a spectrum stored in a reference value memory and of all of the measured values derived therefrom. By means of the manual entry of reference values through the keyboard 11, conversion between the color spaces may also be performed by the computer 63.

In the exemplary embodiment of the invention described, nine different reference values may be stored. Two possibilities are provided in the program of the computer 63 for the selection of the reference value desired in the determination of a reference value or in a comparative measurement. In the first possibility, the number of the reference value is switched manually. The second possibility consists of an automatic selection of the reference value. This is particularly appropriate for the measurement of technical scale inks. The measurement determines the color involved and the corresponding reference value is selected accordingly. For the four scale colors mentioned above, the first four reference numbers of the nine reference memories are reserved.

It is known to those skilled in the art that all photometric measurements are related to white. As both reference to paper and to absolute white are customary, the aforedescribed device stores two reference whites. Measurements with said device permit reference to both of the whites wherein the display may be related to paper white or absolute white, as selected. The white references may be switched manually or automatically. In the display of densitometric values, the computer 63 automatically switches to paper white. In colorimetric and spectral measurements reference is made to absolute white.

The above-mentioned measuring and computing results are passed by the computer 63 through the display control 72 to the display unit 73, which makes it possible in particular to display bar diagrams in densitometry, graphical display of spectra when spectra are being processed, or a measured value in the color space in colorimetry. If comparative measurements are performed, the differences of the measured values are displayed.

In FIG. 3, in the vicinity of the measuring head 4 a lamp monitoring circuit 82 is shown as a block, which serves to monitor the intensity of the light emitted by the lamp 56. For this purpose, a plurality of photodiodes 83, 84 and 85 are provided, of which the photodiode 83 is shown in FIG. 3, while in the detailed block diagram according to FIG. 4, all three photodiodes are shown.

Figure 4:
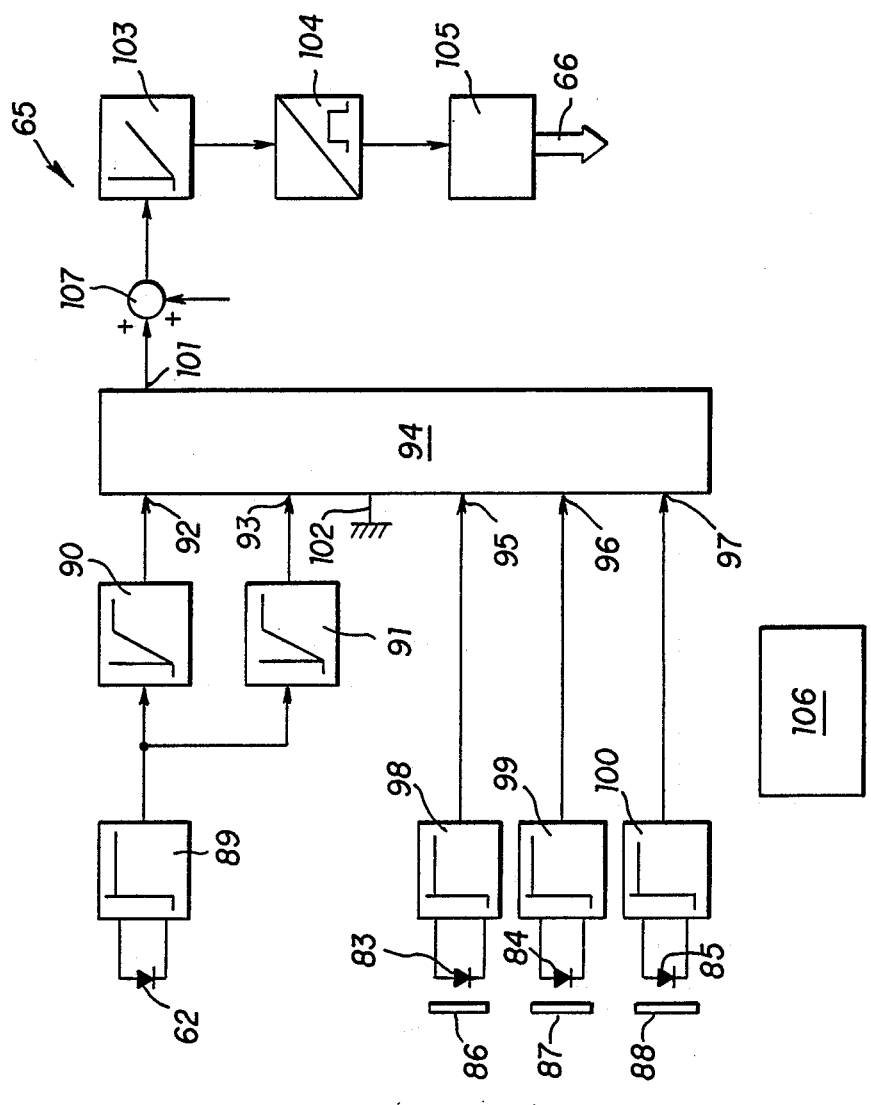

The block diagram shown in FIG. 4 comprises in addition to the lamp monitoring circuit 82, the proportional amplifier 89 corresponding to the amplifier 64 and the analog/digital converter 65. In a realization of the different components according to the block diagram of FIG. 4, the lamp monitoring circuit 82 forms a structural unit with the components connected with the photodiode 62. The photodiode 62 serves to carry out the principal task, i.e. to measure the light spectrally divided by the grating 55. Additionally, the intensity of the lamp 56 must also be monitored to avoid measuring errors. This is performed by the three photodiodes 83, 84, 85 of the lamp monitoring circuit 82, with which filters 86, 87, 88 for red, green and blue are correlated. Each of the photodiodes 83 to 85 thus is used to monitor the lamp at one of three different spectral support locations.

The circuit shown in FIG. 4 makes it possible to measure with high dynamics, as the relative accuracy with "dark" should be approximately equal to the relative accuracy in a "bright" measurement of the spectral light. To be able to carry out the processing of the measured and monitoring data in the computer 63, both the intensity of the measuring light and of the lamp light are digitalized, using the same analog/digital converter in keeping with the block diagram in FIG. 4.

The photodiode 62 supplies a photocurrent to the inlet of a proportional amplifier 89, the outlet voltage of which impacts the inlets of a first hold integrator 90 and a second hold integrator 91. The hold integrators 90 and 91 integrate the outlet voltage of the proportional amplifier 89 and are alternatingly queried and reset.

The outlets of the hold integrators 90 and 91 are connected with the first inlet 92 and the second inlet 93, respectively, of a multiplexer 94. Three further inlets 95, 96, 97 are exposed to lamp light signals derived from the photocurrents of the photodiodes, 83 to 85 and amplified by proportional amplifiers 98 to 100. The multiplexer 94 further comprises an inlet 102 at which a voltage of 0 Volts is standing. The analog multiplexer 94 switches the inlet voltages applied to its inlets 92, 93, 95, 96, 97, 102 alternatingly to its outlet 101, which again alternatingly switches a measuring light signal and an additional lamp light signal to the outlet 101. The switching mode of the multiplexer 94 is thus such that at the outlet 101 the output signals appear in succession in the following order: first hold integrator 90, proportional amplifier 98, second hold integrator 91, proportional amplifier 99, first hold integrator 90, proportional amplifier 100, second hold integrator 91. Subsequently, the inlet 102 exposed to 0 Volts, is switched to the outlet 101. The aforedescribed sequence is then repeated under the control of a separate switching mechanism 106, cycled by the microprocessor of the computer 63.

The hold integrators 90 and 91 maintain their voltage as long as they are switched to the outlet 101. Immediately after that, they are set to 0 by the switching mechanism 106 through a reset inlet, not shown. Integration is being performed whenever one hold integrator 91, 90 or a proportional amplifier 98 to 100 of the lamp monitoring channel are switched to the outlet 101. In this manner the noise of the outlet voltage of the proportional amplifier 89 may be optimally suppressed in the measuring channel.

A constant voltage $U_K$ is added to the outlet voltage at the outlet 101 in an adder 107. The sum impacts an integrator 103, the rise time of which is measured with the aid of a window comparator 104, by measuring the time $t_x$ during which the input signal of the window comparator 104 is within the set window, by means of a counter 105 controlled by the window comparator 104. The counter 105 counts during the time $t_x$ the cycles of a cycle generator, not shown. The state T of the counter at the end of the time $t_x$ is a measure of the photocurrent $I_{PH}$ of the photodiode 62, 83, 84 or 85 selected by the multiplexer 94, wherein:

$T = K1/(K2 + I_{PH})$  $K_1, K_2$: selectable constants.

By the choice of $K_1$ and $K2$ the dynamic and accuracy requirements may be satisfied. The switching mechanism used to coordinate the switching of the multiplexer 94 of the hold integrators 90 and 91 and the integrator 103 is an automatic synchronous state device.

If the photodiode 62 is replaced by a row of diodes, it is possible to eliminate the drive of the diffraction grating 55. In such a case it is appropriate to connect ever diode of the row of diodes by means of a separate amplifier and a multiplexer with the inlet of the analog/digital converter 65. Scanning is then performed by switching the multiplexer.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

We claim:

1. Manual device for the determination of optical reflection properties with a measuring head comprising:
   a source of light;
   optical illumination means to illuminate a measuring surface to be examined by the manual device;
   optical measuring means to capture measuring light reflected by the measuring surface;
   an optoelectronic layout exposed to the measuring light for converting optical signals into data that may be displayed by a display unit, said optoelectronic layout further including a device for spectrally decomposing the measuring light, equipped with a monochromator having a holographic concave reflection grating, together with a layout for detecting and evaluating the spectrum of the measuring light, wherein the grating for scanning of the spectrum is rotated around an axle extending at right angles to an inlet and outlet plane of the measuring light and wherein the spectrally decomposed light impacts a measuring light photodetector, the axle of the grating being permanently, mechanically connected with a drive motor, which is additionally connected with a drive for displacement of the measuring head parallel to a standing surface of the manual device between a rest position and a measuring position.

2. Manual device according to claim 1, wherein the spectrum is scanned by a row of photodiodes.

3. Manual device according to claim 1, wherein the light source is correlated with a plurality of monitoring photodetectors that are sensitive in different spectral ranges, for intensity monitoring.

4. Manual device according to claim 3, wherein the measuring light photodetector and the monitoring photodetectors are connected with an analog/digital converter equipped with a multiplexer, whereby a signal of the measuring light photodetector and one of the monitoring photodetectors is alternatingly selected.

5. Manual device according to claim 4, wherein the measuring light photodetector impacts two hold integrators, which may be queried alternatingly.

6. Manual device according to claim 5, wherein at the end of a multiplexer cycle, a zero voltage inlet of the multiplexer is selected.

7. Manual device according to claim 6, wherein the layout for detecting and evaluating of the spectrum of the measuring light includes a computer, which calculates densitometric or colorimetric values as desired, from the spectra determined.

8. Manual device according to claim 7, wherein the computer contains a non-volatile RAM for storing a state of the manual device, together with calibrating data, and a ROM for storing a program to control the measuring process and for storing different tables.

9. Manual device according to claim 8, wherein comparative measurements with different reference values are carried out.

10. Manual device according to claim 9, wherein said different reference values are variations of white.

11. Manual device according to claim 9, wherein automatic reference value switching as a function of a technical scale color detected, and automatic reference value switching when switching between densitometric and colorimetric values, are provided.

12. Manual device according to claim 8, wherein a maximum density and its spectral position is displayed independently and without specifying a spectral position during a densitometric evaluation of the spectrum.

13. Manual device according to claim 8, wherein switching between different given filter standards is provided during a densitometric evaluation of the spectrum.

14. Manual device according to claim 8, wherein the display unit contains a display field, which makes possible a graphical display of a spectrum, a bar diagram, a color space or the like.

15. Manual device according to claim 8, wherein a manually adjustable filter wheel with a plurality of positions displayable on the display unit is located in the measuring head.

16. Manual device according to claim 15, wherein the filter wheel has three positions in the measuring head, with no filtering taking place in the first position, polarization taking place in the second position and D65 conversion filtering taking place in the third position.

17. Manual device according to claim 8, wherein the device comprises a bi-directional serial interface, whereby the functions of the device may be remotely controlled and may be called up and output relative to measured values detected and calculated.

18. Manual device according to claim 1, wherein the device is equipped with a rechargeable battery supplying a voltage transformer for producing supply voltages required for operating electric and electronic components, and wherein an automatic synchronous device is provided for controlling analogous monitoring circuits and for actuating and deactivating different structural units, whereby a principal power source is turned off after about 0.1 to 1.5 seconds and the display unit is turned off after about 30 seconds to save power, while a keyboard, a serial interface and a non-volatile memory remain on.

19. Manual device according to claim 1, wherein the layout for detecting and evaluating of the spectrum of the measuring light includes a computer, which calculates densitometric or colorimetric values as desired, from the spectra determined.

20. Manual device according to claim 19, wherein the computer contains a non-volatile RAM for storing a state of the manual device, together with calibrating data, and a ROM for storing a program to control the measuring process and for storing different tables.

21. Manual device according to claim 20, wherein comparative measurements with different reference values are carried out.

22. Manual device according to claim 21, wherein automatic reference value switching as a function of a technical scale color detected, and automatic reference value switching when switching between densitometric and colorimetric values, are provided.

23. Manual device according to claim 1, wherein the display unit contains a display field, which makes possible a graphical display of a spectrum, a bar diagram, a color space or the like.

24. Manual device according to claim 1, wherein a manually adjustable filter wheel with a plurality of positions displayable on the display unit is located in the measuring head.

25. Manual device according to claim 24, wherein the filter wheel has three positions in the measuring head, with no filtering taking place in the first position, polarization taking place in the second position and D65 conversion filtering taking place in the third position.

26. Manual device according to claim 17, wherein the device comprises a bi-directional serial interface, whereby the functions of the device may be remotely controlled and may be called up and output relative to measured values detected and calculated.

* * * * *